(12) United States Patent
Bodor et al.

(10) Patent No.: US 9,572,552 B1
(45) Date of Patent: Feb. 21, 2017

(54) BATTERY PACK FOR POWER SURGICAL HAND PIECE WITH HEAT DISSIPATING MEANS

(71) Applicant: Integrated Medical Systems International, Inc., Birmingham, AL (US)

(72) Inventors: Peter Pal Bodor, Pembroke Pines, FL (US); Leighton Schonlau, Weston, FL (US); Craig Glenn Bishop, Boca Raton, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 747 days.

(21) Appl. No.: 13/963,337

(22) Filed: Aug. 9, 2013

Related U.S. Application Data

(60) Provisional application No. 61/681,218, filed on Aug. 9, 2012.

(51) Int. Cl.
*H01M 10/623* (2014.01)
*H01M 10/6572* (2014.01)
*A61B 17/00* (2006.01)

(52) U.S. Cl.
CPC .................................... *A61B 17/00* (2013.01)

(58) Field of Classification Search
CPC ........ H01M 10/46; H01M 10/60; A61B 17/00
USPC ........................................ 429/96–100, 120
See application file for complete search history.

(56) References Cited

U.S. PATENT DOCUMENTS

| | | | | |
|---|---|---|---|---|
| 6,664,000 | B1 * | 12/2003 | Sonobe | H01M 2/34 429/100 |
| 2005/0202310 | A1 * | 9/2005 | Yahnker | B25F 5/008 429/62 |
| 2006/0110657 | A1 * | 5/2006 | Stanton | H01M 2/1072 429/120 |
| 2007/0236177 | A1 * | 10/2007 | Phillips | H01M 2/0202 320/115 |
| 2008/0311466 | A1 * | 12/2008 | Yang | H01M 10/486 429/62 |
| 2011/0300420 | A1 * | 12/2011 | Johnson, Jr. | H01M 10/633 429/62 |

* cited by examiner

*Primary Examiner* — James Lee
(74) *Attorney, Agent, or Firm* — C. Brandon Browning; Maynard, Cooper & Gale, PC

(57) ABSTRACT

A battery powered surgical handpiece system including a surgical instrument having a housing containing a motor and a motor controller portion, and a battery pack configured for detachably coupling to the surgical instrument, the battery pack including a thermoelectric cooler. The thermoelectric cooler is directly thermally coupled between the motor controller portion and a thermally conductive element supported by the battery pack, the thermally conductive element being movable between a first position where the thermally conductive element is spaced apart from an internal housing of the battery pack and a second position where the thermally conductive element is thermally coupled to and between an external housing of the battery pack and the internal housing of the battery pack.

11 Claims, 9 Drawing Sheets

BATTERY PACK FOR POWER SURGICAL HAND PIECE WITH HEAT DISSIPATING MEANS

RELATED APPLICATION

This application claims priority to U.S. Patent Application Ser. No. 61/681,218, filed on Aug. 9, 2012, and titled, "Battery Pack For Power Surgical Hand Piece With Heat Dissipating Means," the entire contents of which are incorporated herein by reference.

FIELD OF INVENTION

The present invention relates to battery packs for power surgical hand pieces, and more particularly, to powered surgical instruments systems including battery backs that are configured for selectively directing heat away from surgical instruments and into the battery packs and out of the battery packs into the environment or a heat sink such as a battery charging station.

BACKGROUND OF INVENTION

A typical cordless handheld surgical instrument uses a detachable and rechargeable battery pack to power the instrument. In most instances, the battery pack is attached to a bottom or base portion of the housing of the instrument. The housing or a motor controller module, which is contained within a handgrip portion of the housing, supports electrical contacts configured for coupling to the battery pack and delivering power through the motor controller module to the motor. Trigger controls, also contained within the handgrip portion of the housing, interface with the motor controller module for selectively delivering the power from the battery pack to the motor. In most instances, the motor control module is in close proximity to the electrical contacts of the instrument, for example, as illustrated in U.S. Pat. No. 7,638,958 to Philipp et al.

The motor controller module generally includes a processor portion and a power transmission portion. The power transmission portion is commonly composed of metal-oxide-semiconductor field-effect transistors (MOSFETs) which generate a large amount of heat during operation. This heat, in combination with the heat generated by the motor, can raise temperatures within the housing to 120 degrees C. or more. At these temperatures, the instrument's sensitive electronic circuitry, such as the circuitry of the motor control module, can suffer heat damage. If the heat is great enough, the heat can be transferred into the hand grip in sufficient amounts to cause discomfort for the operator of the device. Thus, a common failure mode in cordless, powered handheld surgical instruments is the over-heating of controller electronic components due to heat generated by the components, heat sensitivity of the components and the lack of an efficient means by which heat is dissipated from the controller module. To address the overheating of cordless handheld surgical instruments U.S. Pat. No. 7,211,347 to Sugiura et al. and U.S. Pat. No. 6,933,076 to Ura et al. describe equipping a battery housing with fins which function as a heat sink and heat spreader for the battery cells therein.

SUMMARY OF THE INVENTION

The present invention relates to a battery pack for powered surgical handpieces, the battery pack having an outer housing configured to serve as a heat sink and heat dissipating means for heat generated by the handpiece components such as the MOSFETs and motor. The outer housing is further configured to deter or slow heat transfer into the battery cells of the battery pack by sealing the battery cells within an inner housing which is spaced apart and insulated from the outer housing In particular, the outer battery housing acts as a heat spreader for a surgical component adjacent to the battery pack, where physical and thermal contact exists between the battery pack outer housing and the component. Such a design can be applied to battery powered surgical handpieces including drills, reamers, saws and the like.

According to one aspect of the invention, there is provided battery powered surgical handpiece system including a surgical instrument including an instrument housing having a handgrip portion, a motor and a motor controller portion operatively coupled to the motor, the motor controller portion being at least partially contained within and essentially thermally isolated from the handgrip portion. The system further includes a battery pack that is configured for detachably coupling to the surgical instrument, the battery pack including an internal housing that is essentially thermally isolated from an external housing of the battery pack. In use, when the battery pack is operatively coupled to the surgical instrument, the external housing of the battery pack is directly and thermally coupled to the motor controller portion thereby allowing the direct transfer of heat from the motor controller portion to the external housing of the battery pack where the heat is dissipated to the environment through a number of external fins.

So that heat generated within the battery cells during charging operations may be quickly removed from the battery pack, the system may also include a thermally conductive element supported by the outer housing of the battery pack that is movable between a first position, where the thermally conductive element is spaced apart from the internal housing of the battery pack and a second position, where the thermally conductive element is directly thermally coupled to and between the external housing of the battery pack and the internal housing of the battery pack. A bias member may be arranged to selectively maintain the thermally conductive element in the first position. When coupled to the charging station, the thermally conductive element compressed and converted to the second position so that heat generated by the battery cells during charging operation can be transferred from the internal housing through the thermally conductive element and to the charging station or to the external battery housing where the heat is dissipated to the environment through the fins.

According to another aspect of the invention, there is provided a battery powered surgical hand piece system including a surgical instrument having a housing containing a motor and a motor controller portion, and a battery pack configured for detachably coupling to the surgical instrument, the battery pack including a thermoelectric cooler. The thermoelectric cooler is directly thermally coupled between the motor controller portion and a thermally conductive element supported by the battery pack, the thermally conductive element being movable between a first position, where the thermally conductive element is spaced apart from an internal housing of the battery pack, and a second position where the thermally conductive element is thermally coupled to and between an external housing of the battery pack and the internal housing of the battery pack, preferably with the battery cells being thermally insulated so the heat pulled from the hand piece does not interfere with the battery cells' performance. A microcontroller-controlled actuator can be provided for selectively actuating the thermally conductive element between the first position when it is desired to transfer heat from the instrument to the battery pack and the second position when it is desired to transfer heat generated within the battery cells during charging operations through the external housing to the environment or to a charging station. The microcontroller monitors the temperature of the hand piece, the temperature of the heat sink in the battery and the battery power level in a control loop to optimize heat transfer for best performance of the entire hand piece/battery block system.

According to another aspect of the invention, there is provided a battery powered surgical handpiece system including a battery pack configured for detachably coupling to a surgical instrument, the battery pack containing a thermoelectric cooler. The thermoelectric cooler is arranged to be thermally coupled between a motor controller portion of the surgical instrument and the battery pack when the battery pack is operatively coupled to the surgical instrument. The thermoelectric cooler may supported on a thermally conductive element that is slidably arranged within the battery pack between a first position where the thermally conductive element is spaced apart from an internal housing of the battery pack and a second position where the thermally conductive element is directly thermally coupled to and between the internal housing and an external housing of the battery pack.

According to yet another aspect of the invention, there is provided a control system and method for a battery powered surgical handpiece including a microcontroller that is embedded in a battery pack and powered by the battery pack's power cells. When the battery pack is attached to the surgical handpiece, the battery pack's microcontroller constantly monitors the voltage and the capacity of the power cells and the temperature of the handpiece, either through a data interface or directly from a thermal sensor placed at the battery pack and/or handpiece/battery pack interface. When the firmware running in the microcontroller determines that the temperature is too high in the handpiece it mechanically engages a thermal interface with the handpiece to draw heat away from the handpiece and into a thermal sink located in the battery pack which is thermally isolated from the power cells in the battery. Typically, the heat sink is located outside of the power cells so the heat is dissipated via convection to the environment, for example, via an external battery pack housing. Alternatively, the battery charger can be arranged to pull the heat away from it and dissipate it using a fan or similar means. The firmware in the microcontroller can also monitor the power or capacity in the power cells to determine whether to activate the mechanical thermal interface, or the firmware can use some of the power cells' power to actively draw heat away from the handpiece and into the battery pack's thermal sink using thermoelectric means such as a Peltier Junction or similar device. Additionally, the microcontroller monitors the handpiece temperature and the thermal sink temperature. Relying the these temperatures, an algorithm is provided in the system for determining the optimal duty cycle for energizing the thermoelectric heat sinking process to provide optimal heat transfer for the handpiece.

DETAILED DESCRIPTION OF PRESENTLY PREFERRED EMBODIMENTS

Figure 1:
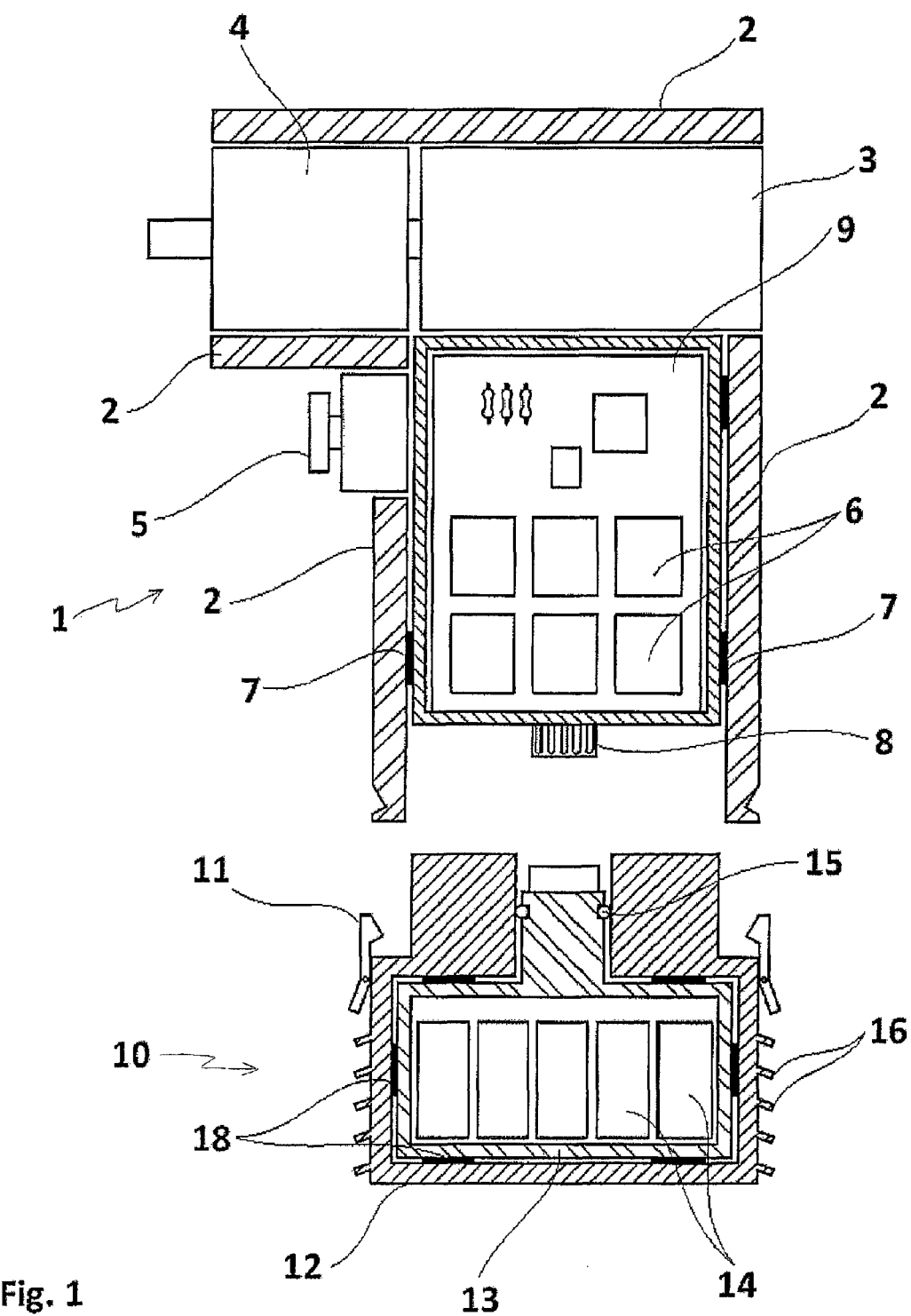
FIG. 1 is a sectional view of a surgical handpiece and a battery pack of a battery powered surgical handpiece system in accordance with a preferred embodiment of the present invention.
Figure 2:
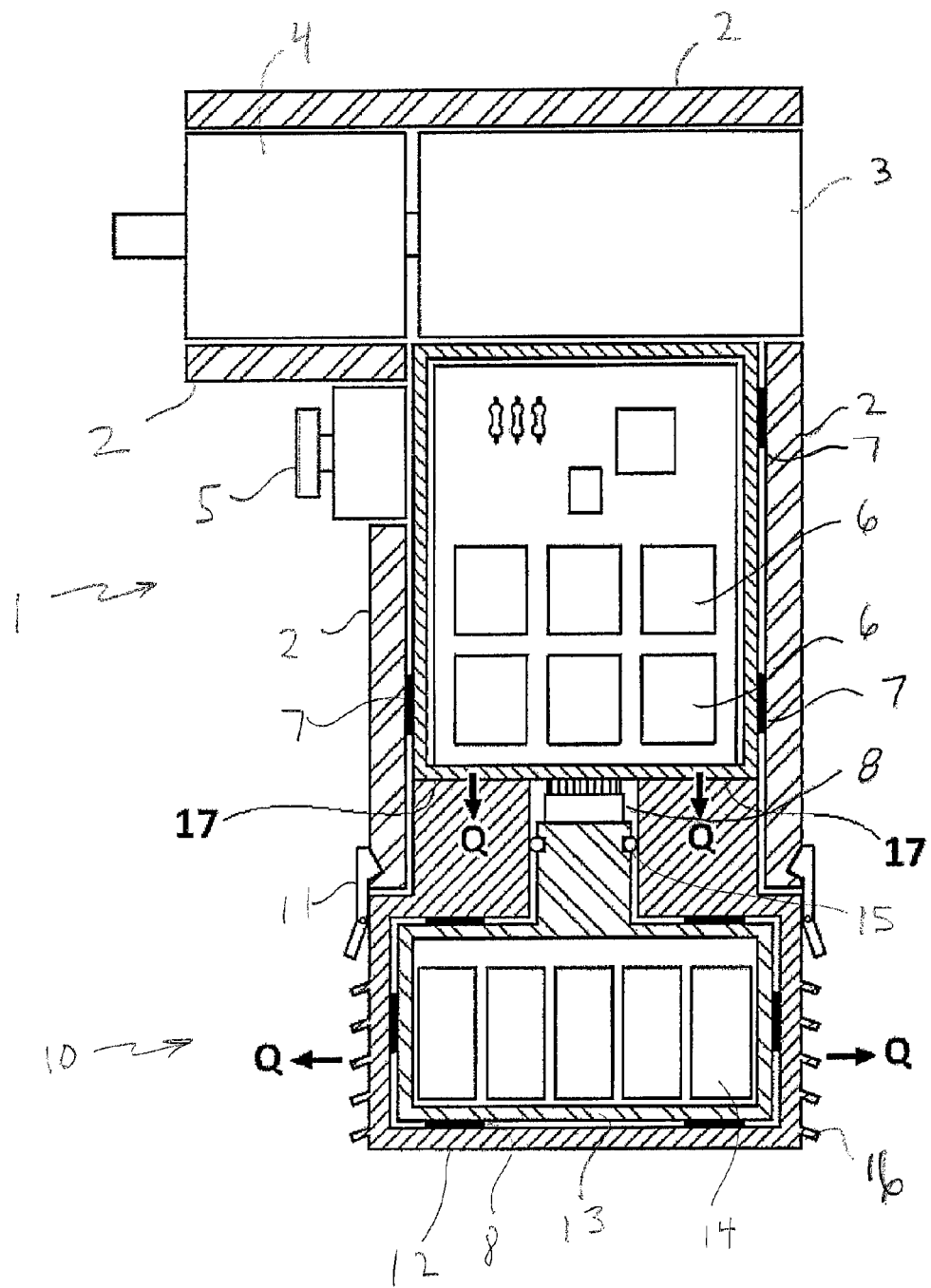
FIG. 2 is a sectional view of the battery powered surgical handpiece system of FIG. 1 showing the surgical handpiece operatively coupled to the battery pack.
Figure 3:
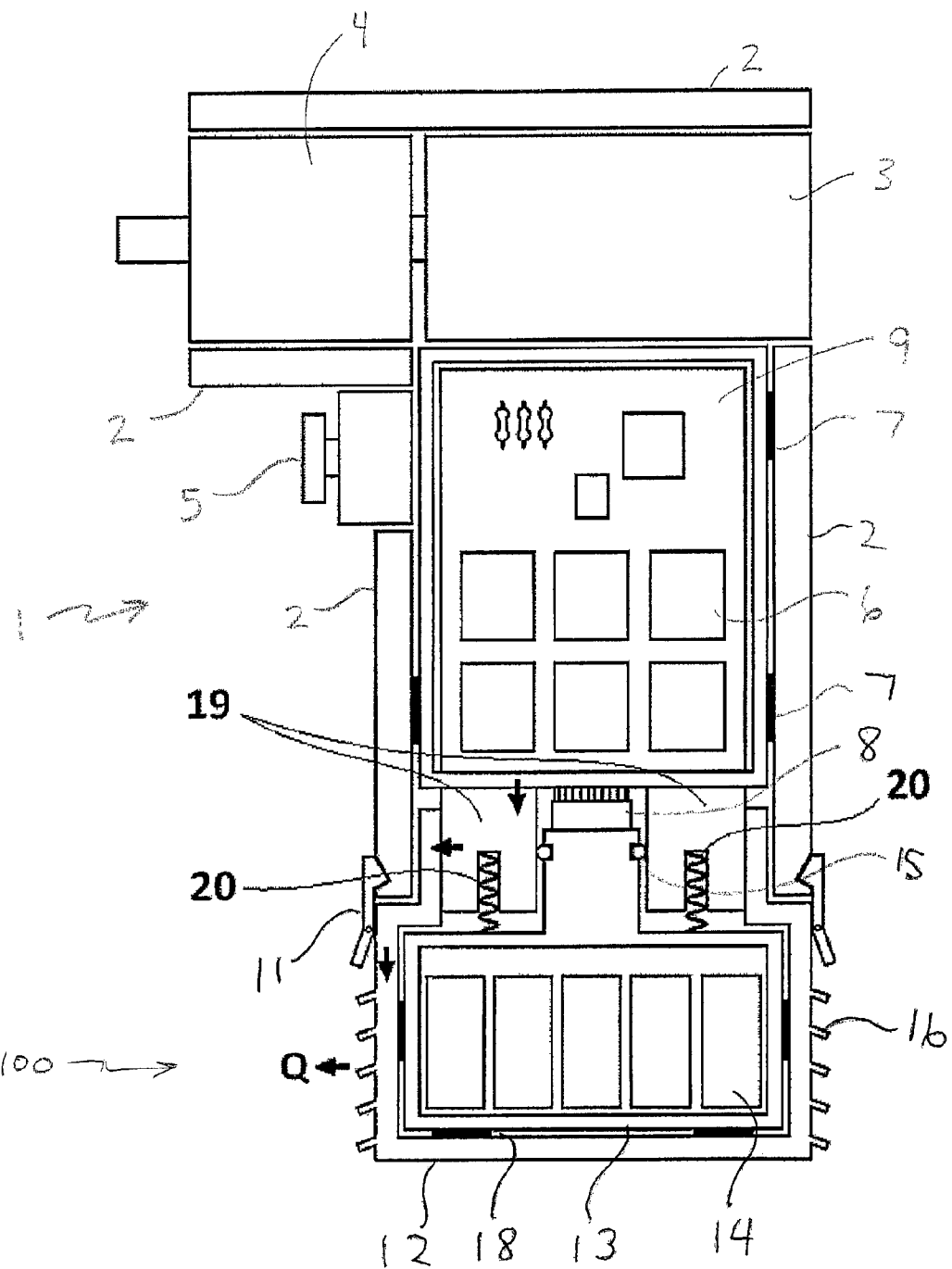
FIG. 3 is a sectional view of a surgical handpiece and a battery pack of a battery powered surgical handpiece system in accordance with another preferred embodiment of the present invention.
Figure 4:
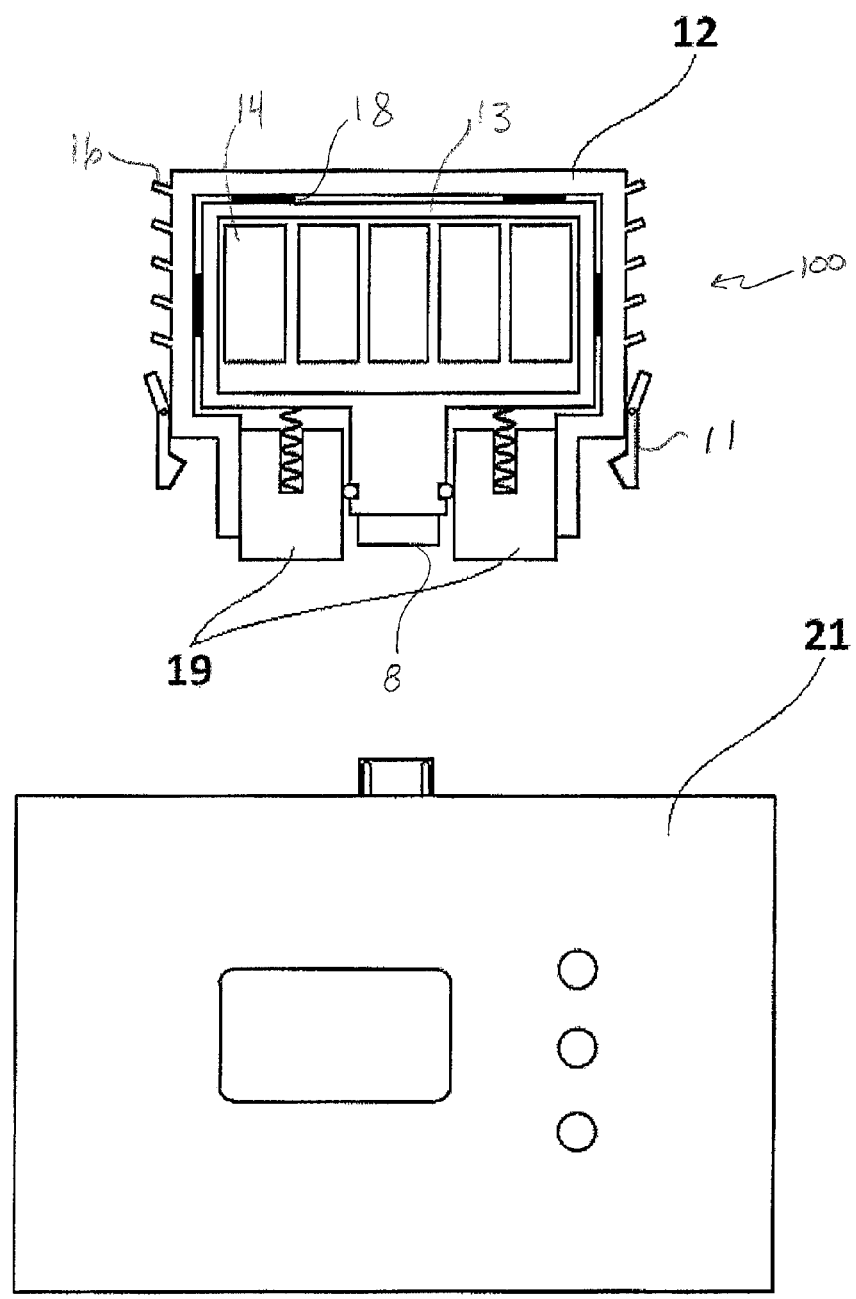
FIG. 4 is a sectional view of the battery pack of FIG. 4 immediately prior to the battery pack being operatively coupled to a charging station.
Figure 5:
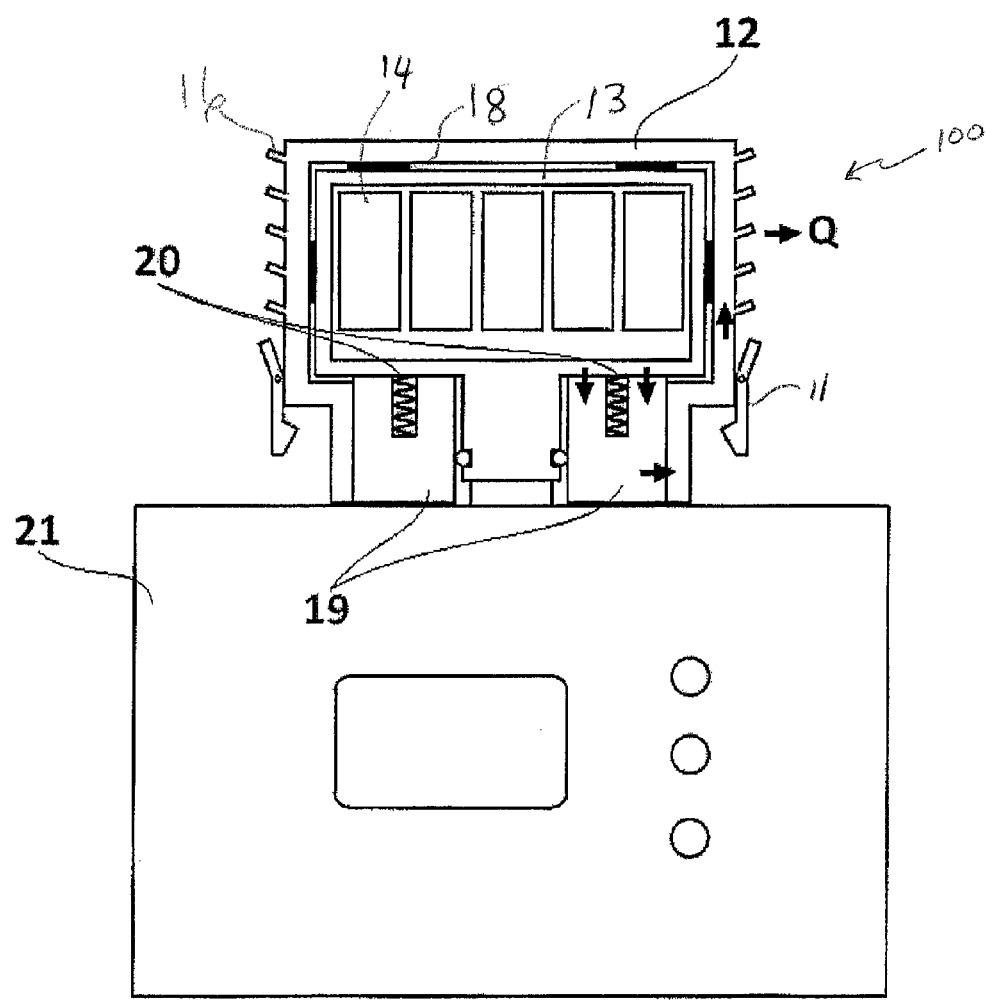
FIG. 5 is a sectional view of the battery pack and charging station of FIG. 4 being operatively coupled.
Figure 6:
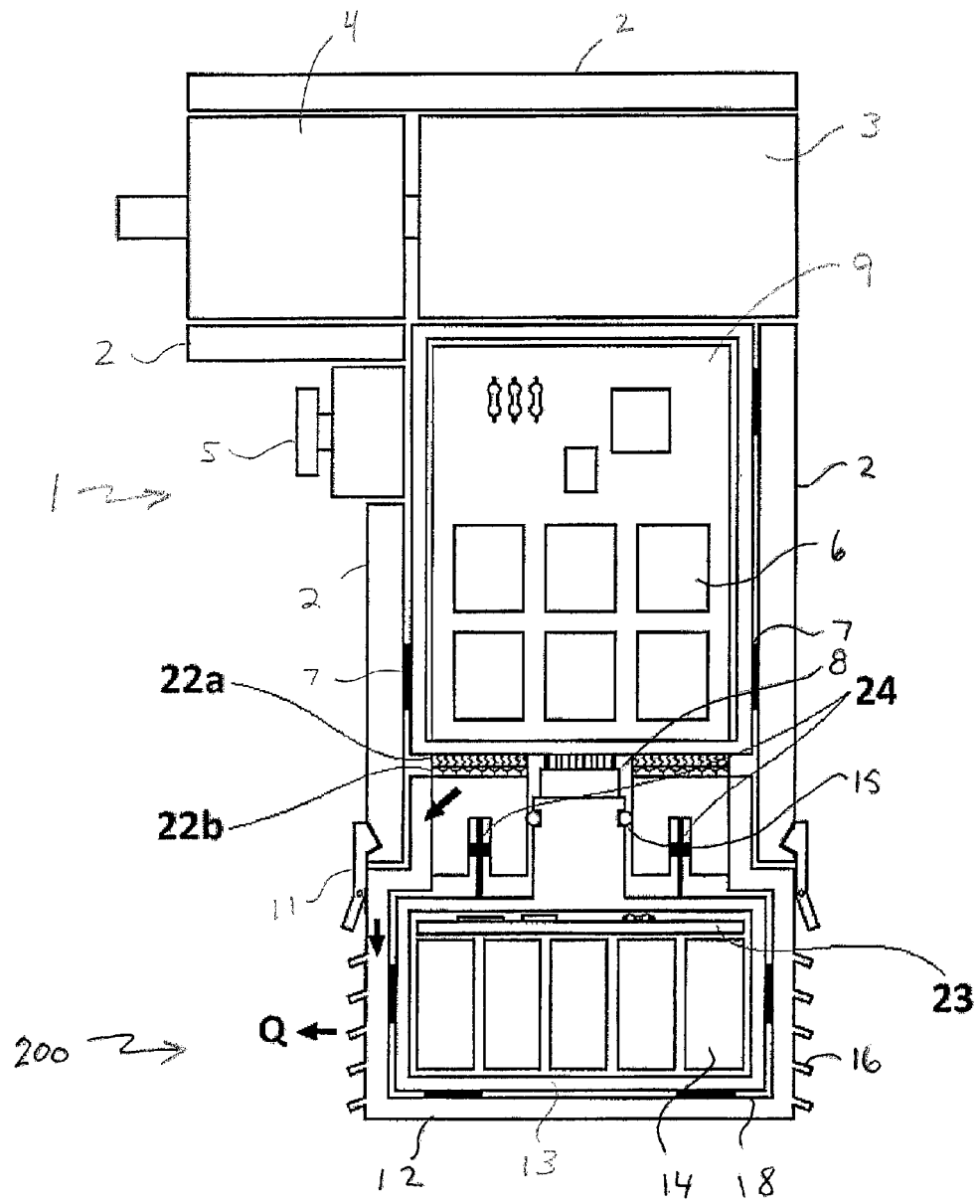
FIG. 6 is a sectional view of a battery powered surgical handpiece system in accordance with yet another preferred embodiment of the present invention showing a thermally conductive element in a first position.
Figure 7:
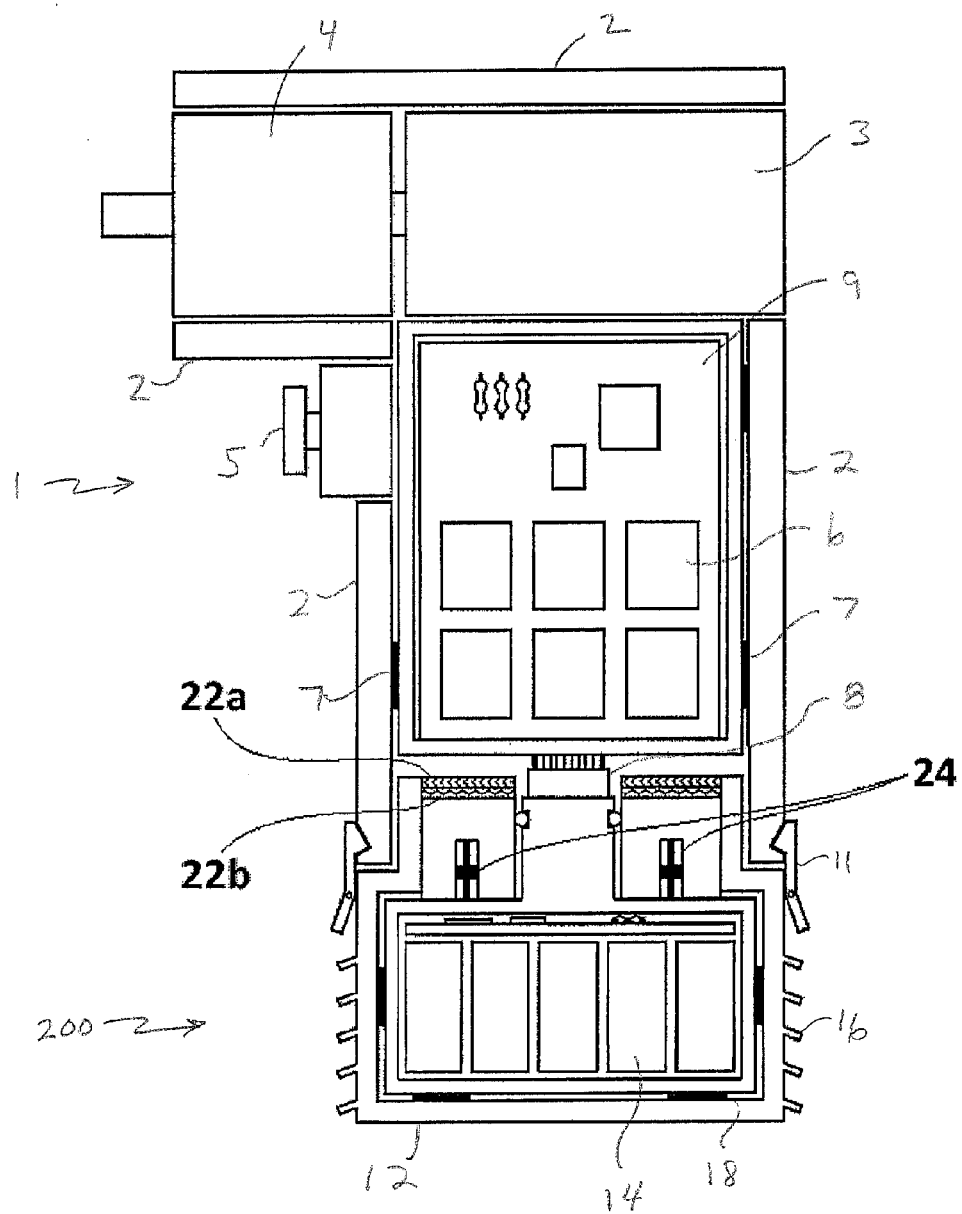
FIG. 7 is sectional view of the battery powered surgical handpiece system of FIG. 6 showing the thermally conductive element in a second position.
Figure 8:
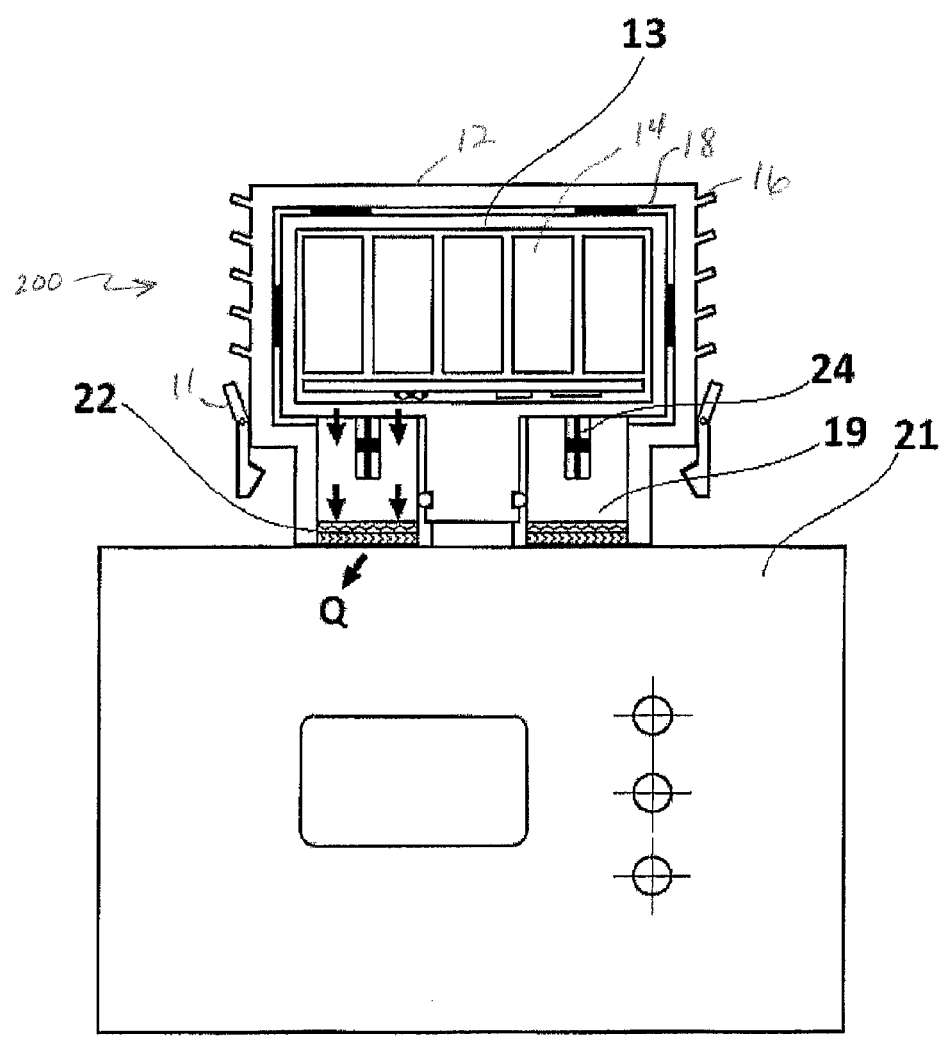
FIG. 8 is a sectional view of a battery pack of the battery powered surgical handpiece system of FIG. 6 operatively coupled to a charging station.
Figure 9:
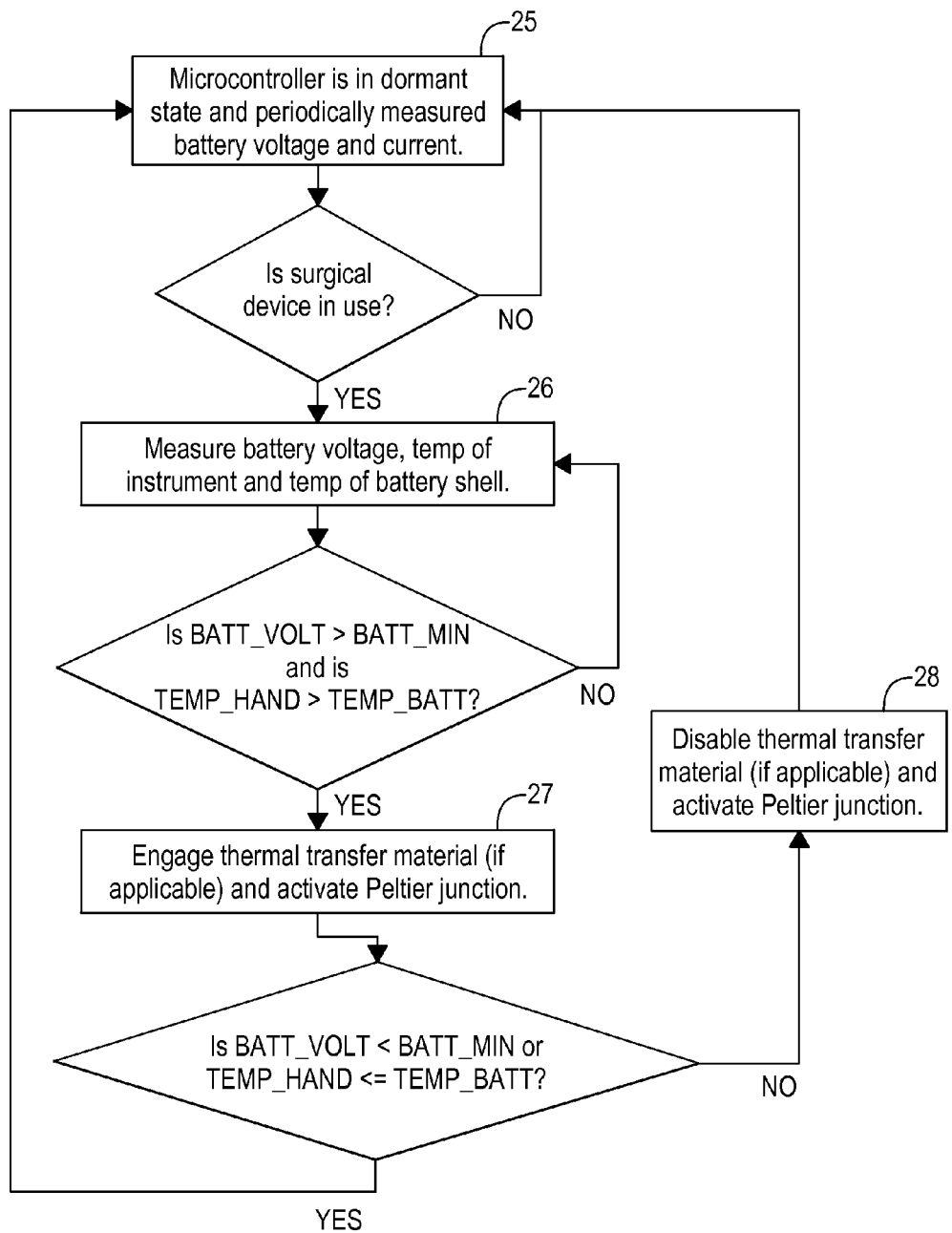
FIG. 9 is a flow chart illustrating the control of a thermoelectric cooler of the battery powered surgical handpiece system of FIG. 6 by a microcontroller.

The preferred embodiments of the present invention are illustrated in FIGS. 1 through 9, where like portions share like numbering. In particular, FIGS. 1 and 2 depict a battery powered surgical handpiece system in accordance with a first embodiment of the present invention. FIGS. 3 through 5 depict a battery powered surgical handpiece system in accordance with a second embodiment of the present invention, the system including a battery pack containing a thermally conductive element that is slidable between a first position for transferring heat from a surgical instrument to an external battery pack housing and a second position for transferring heat from an internal battery pack housing to the external housing and into the environment. FIGS. 6 through 9 depict a battery powered surgical handpiece system in accordance with a third embodiment of the present invention, the system including a battery pack containing a thermoelectric cooler supported on a thermally conductive element that is slidable between a first position for transferring heat from a surgical instrument to an external battery pack housing and a second position for transferring heat from an internal battery pack housing through the thermoelectric cooler and into a heat sink such as a charging station. A benefit of this arrangement is that the battery can be charged faster, more efficiently and at the battery chemistry's optimal temperature which increases the battery's service life. FIG. 9 depicts a control logic for the thermoelectric cooler of the third embodiment of the present invention.

Referring to FIGS. 1 and 2, the first embodiment of a battery powered surgical handpiece system includes a surgical handpiece 1 having a housing 2. Housing 2 contains an electric motor 3, a gear train 4 operatively coupled to the motor, a trigger 5 for selectively supplying power to the motor and a motor controller unit 9. Motor controller unit 9 includes a processor, a bank of MOSFETs 6 for transporting electricity from a power source to the motor and a lead pad 8 for electrically coupling the power source to the motor controller unit. To prevent heat generated by MOSFETs 6 from overheating a handgrip portion of housing 2, motor controller unit 9 is thermally isolated from handpiece housing 2 using insulating pads 7 which maintain motor controller unit 9 spaced apart from an inner wall of housing 2 and thereby separated by an insulating air space. Separation of motor controller unit 9 from housing 2 with insulating pads 7 and the air space essentially thermally isolates motor controller unit 9 from housing 2.

A battery pack 10 for powering surgical handpiece 1 is also provided. Battery pack 10 includes an outer housing 12 with latching elements 11 configured for detachably coupling the battery pack to handpiece 1 and heat dissipating fins 16. Battery pack 10 further includes an internal housing 13 containing battery cells 14. Internal 13 housing and external housing 12 are made of good thermally conductive materials. Internal housing 13 is spaced apart and essentially thermally isolated from external housing 12 using insulating pads 18 and is sealed within external housing 12 by sealing elements 15.

Referring to FIG. 2, when battery pack 10 is operatively coupled to handpiece 1, external housing 12 makes direct physical and thermal contact with motor controller 9 at surfaces 17. In particular, controller unit 9 has a lower edge that is equipped with thermal contact surfaces 17. Surfaces 17 are made of a highly conductive material such as copper or aluminum. Surfaces 17 are positioned in close proximity to MOSFETs 6 supported on motor controller unit 9. When battery pack 10 attaches to handpiece body 1, external housing 12 partially extends into the handpiece 1, and external housing 12 makes thermal contact with motor controller unit 9 at surfaces 17. During normal operation of the handpiece, motor controller 9 heats up and creates a temperature gradient with battery housing 12 causing heat Q from controller unit 9 to flow into battery housing 12 through surfaces 17. Q indicates the path of heat transfer. Heat Q then dissipates into the environment via convection through fins 16 or other geometries to increase surface area.

Battery pack 10 may be a non-removable type, in which case the thermal contact between battery external housing 12 and motor controller unit 9 may be a permanent one and may include a single, integral thermal contact portion located between the controller unit and the battery pack. In applications where heating and warming of battery cells 14 are not critical, the battery housing may be in thermal contact with the cells, the cells acting as a heat sink, by way of its mass, to store heat transferred from the controller unit. In applications where heating of cells 14 is not desirable, the cells may be thermally isolated from the battery housing and/or controller unit.

Referring to FIGS. 3 through 5, the second embodiment of a battery powered surgical handpiece system includes a surgical handpiece 1 having a housing 2. Housing 2 contains an electric motor 3, a gear train 4 operatively coupled to the motor, a trigger 5 for selectively supplying power to the motor and a motor controller unit 9. Motor controller unit 9 includes a processor, a bank of MOSFETs 6 for transporting electricity from a power source to the motor and a lead pad 8 for electrically coupling the power source to the motor controller unit. To prevent heat generated by MOSFETs 6 from overheating a handgrip portion of housing 2, motor controller unit 9 is thermally isolated from handpiece housing 2 using insulating pads 7 which maintain motor controller unit 9 spaced apart from an inner wall of housing 2 and thereby separated by an insulating air space. Separation of motor controller unit 9 from housing 2 with insulating pads 7 and the air space essentially thermally isolates motor controller unit 9 from housing 2.

A battery pack 100 for powering surgical handpiece 1 is also provided. Battery pack 100 includes an outer housing 12 with latching elements 11 configured for detachably coupling the battery pack to handpiece 1 and heat dissipating fins 16. Battery pack 100 further includes an internal housing 13 containing battery cells 14. Internal housing 13 and external housing 12 are made of good thermally conductive materials. Internal housing 13 is spaced apart and essentially thermally isolated from external housing 12 using insulating pads 18 and is sealed within external housing 12 by sealing elements 15.

Battery pack 100 further includes a sliding element 19 made of a good thermally conductive material that is supported within battery pack 100 by an elastic member 20 that is biased against an outside surface of internal housing 13. In use, when coupled to handpiece 1, sliding element 20 is pressed against controller unit 9 making direct contact with both motor controller unit 9 and battery external housing 12 thereby thermally coupling motor controller unit 9 and external battery housing 12. Heat Q from controller unit 9 flows into sliding element 19 through battery external housing 12 to fins 16 where the heat dissipates to the environment through convection. Arranged in this manner, sliding element 20 is spaced apart from and essentially thermally isolated from internal battery housing 13.

The second embodiment of a battery powered surgical handpiece system further includes a charging station 21 which can act as a heat sink for cooling battery pack 100 during charging operations. When battery pack 100 is coupled to charging station 21, elastic support elements 20 compresses, causing sliding element 19 to change position within the battery pack and thermally couple battery internal 13 housing with external 12 housings. Thus, during charging cycles, heat Q generated in battery cells 14 can flow through internal housing 13 to sliding element 19 and through external housing 12 before dissipating to the environment through fins 16 or into charging station 21, which acts as a heat sink.

Referring to FIGS. 3 through 5, the third embodiment of a battery powered surgical handpiece system includes a surgical handpiece 1 having a housing 2. Housing 2 contains an electric motor 3, a gear train 4 operatively coupled to the motor, a trigger 5 for selectively supplying power to the motor and a motor controller unit 9. Motor controller unit 9 includes a processor, a bank of MOSFETs 6 for transporting electricity from a power source to the motor and a lead pad 8 for electrically coupling the power source to the motor controller unit. To prevent heat generated by MOSFETs 6 from overheating a handgrip portion of housing 2, motor controller unit 9 is thermally isolated from handpiece housing 2 using insulating pads 7 which maintain motor controller unit 9 spaced apart from an inner wall of housing 2 and thereby separated by an insulating air space. Separation of motor controller unit 9 from housing 2 with insulating pads 7 and the air space essentially thermally isolates motor controller unit 9 from housing 2.

A battery pack 200 for powering surgical handpiece 1 is also provided. Battery pack 200 includes an outer housing 12 with latching elements 11 configured for detachably coupling the battery pack to handpiece 1 and heat dissipating fins 16. Battery pack 200 further includes and an internal housing 13 containing battery cells 14. Internal housing 13 and external housing 12 are made of good thermally conductive materials. Internal housing 13 is spaced apart and essentially thermally isolated from external housing 12 using insulating pads 18 and is sealed within external housing 12 by sealing elements 15.

Battery pack 200 further includes thermoelectric coolers 22, such as Peltier Junction devices, each having a hot side 22a and cold side 22b. Each of thermoelectric coolers 22 is supported on an outer end of a sliding element 19 that is held within the battery pack. Sliding element 19 is selectively actuated by actuators 24 and controlled a circuit board 23 containing a micro controller PCB 23 having microcontroller with embedded firmware for control and temperature sensor operations.

In use, each sliding element 19 is caused to thermally engage motor controller unit 9 through a thermoelectric cooler 22 by the action of actuators 24 directing sliding member 19 toward the motor controller unit so that hot side 22a of the thermoelectric cooler contacts the motor controller unit. The temperature gradient between the motor controller unit and the sliding element is increased by the action of the thermoelectric cooler thereby increasing the rate of heat flow from the motor controller unit to the sliding element. In this manner, thermoelectric coolers 22 direct heat away from housing 2 and motor controller unit 9 of surgical device 1 into external battery housing 12 by creating an active thermal gradient using the battery pack's power. The firmware algorithm determines the optimal movement of heat transfer based on the available battery power, temperature of motor controller unit 9, temperature of battery pack 200, and the specifications of thermoelectric cooler 22.

Referring to FIG. 8, there is depicted sliding element 19 arranged to thermally couple internal battery housing 13 with a charging station 21 while thermoelectric cooler 22 is activated in reversed polarity. Pursuant to this arrangement, heat is removed from battery cells 14 during charging of battery pack 200, and the heat is conducted into charging station 21 for dissipation (fan, convection heat radiators, or other method known in the art). This occurs by sliding element 19 thermally coupling internal battery housing 13 with charging station 21 while thermoelectric cooler 22 is activated in reversed polarity thereby creating a hot side junction at the battery pack side and cold side junction at the charger side for promoting heat transfer from battery cells 14 to charging station 21. This allows for faster battery charging and longer battery life due to improved heat transfer during charging.

Referring to FIG. 9, there is depicted a control method for operating the thermally conductive sliding element 9 and thermoelectric cooler 22. Generally, the process includes measuring the battery voltage, available battery power, temperatures of the surgical instrument and the battery housing and determining the optimal method to transfer excess heat to provide optimal operation and heat transfer across the surgical device and battery pack. More particularly, this process includes reverting the microcontroller to dormant mode 25 upon detection of battery removal (or idle mode of surgical device). In dormant mode 25, all heat transfer controls and measurements are discontinued to allow the surgical tool and/or battery to radiate the excess heat through normal convection methods. This typically draws less power than the self-leakage of battery cells 14. The microcontroller switches to active monitoring mode 26 when the voltage drop and current draw indicate that surgical instrument 1 is being used. At this point, the microcontroller measures the temperature of the hand grip area of housing 2 (or thermally conductive material 17 attached to motor controller/driver unit 9) and battery housing 12 housing and 13 using thermistors or similar temperature measuring devices. Upon measuring a pre-determined temperature difference, the microcontroller is used to elevate 27 the position of the sliding element 19 using an electro-mechanical device 27 such as a solenoid, motor, or other actuators 24 to bring the sliding element into contact with the motor controller unit 9. The microcontroller also energize 27 thermoelectric cooler or Peltier junction 22 to direct heat away from motor controller unit 9 area and transfer the heat to external battery housing 12 through sliding element 19. The microcontroller then monitors the power of battery pack 200 and the current drain during this heat transfer operation to allow surgical instrument 1 to operate within predetermined specifications while preventing over-discharging of battery cells 14. When appropriate, the microcontroller retracts 28 and disengages sliding element 19 from motor controller unit 9 and deactivates thermoelectric cooler 22.

As will be apparent to one skilled in the art, various modifications can be made within the scope of the aforesaid description. Such modifications being within the ability of one skilled in the art form a part of the present invention and are embraced by the claims below.

What is claimed:

1. A battery powered surgical handpiece system comprising:
    a surgical instrument including a housing containing a motor and a motor controller portion, and
    a battery pack configured for detachably coupling to the surgical instrument, the battery pack including a thermoelectric cooler,
    wherein, when the battery pack is operatively coupled to the surgical instrument, the thermoelectric cooler is thermally coupled between the motor controller portion and a thermally conductive element supported by the battery pack, the thermally conductive element being movable between a first position where the thermally conductive element is spaced apart from an internal housing of the battery pack and a second position where the thermally conductive element is thermally coupled to and between an external housing of the battery pack and the internal housing of the battery pack, and
    wherein the battery pack further includes a microcontroller-controlled actuator configured for selectively actuating the thermally conductive element between the first position and the second position.

2. The system of claim 1 wherein the battery pack further includes a microcontroller with embedded firmware configured for energizing the thermoelectric cooler for creating temperature gradient between the battery pack and motor controller portion.

3. The system of claim 1 wherein the thermoelectric cooler is a Peltier junction device.

4. The system of claim 1 further comprising a charging station, wherein when the battery pack is operatively coupled to the charging station, the thermoelectric cooler is thermally coupled between the battery pack and the charging station and the thermally conductive element is in the second position.

5. A method of transferring heat generated by the surgical instrument and the battery pack of claim 4 comprising coupling the battery pack to the surgical instrument, creating a first flow of heat from the motor controller portion through the thermally conductive element to the external housing of the battery pack while the thermally conductive element is in the first position, detaching the battery pack from the surgical instrument, attaching the battery pack to the charging station whereby the thermally conductive element is converted to the second position, and creating a second flow of heat from the battery pack to the charging station.

6. A battery powered surgical handpiece system comprising:
   a battery pack configured for detachably coupling to a surgical instrument, the battery pack including a thermoelectric cooler,
   wherein, when the battery pack is operatively coupled to the surgical instrument, the thermoelectric cooler is thermally coupled between a motor controller portion of the surgical instrument and the battery pack, and
   wherein the thermoelectric cooler is supported on a thermally conductive element that is slidably arranged within the battery pack.

7. The system of claim 6 wherein the thermally conductive element is slidable between a first position where the thermally conductive element is spaced apart from an internal housing of the battery pack and a second position where the thermally conductive element is directly thermally coupled to and between the internal housing and an external housing of the battery pack.

8. The system according to claim 7 wherein, when the battery pack is attached to the surgical instrument, the thermally conductive element is in the first position and when the battery pack is attached to a charging station, the thermally conductive element is in the second position.

9. The system according to claim 6 further comprising an instrument operatively coupled to the battery pack, the instrument being selected from the group consisting a drill, a saw and a reamer.

10. A method of transferring heat using the surgical instrument of claim 6 comprising coupling the battery pack to the surgical instrument, thermally coupling the thermoelectric cooler to the motor controller portion, providing the thermoelectric cooler with a first polarity, and creating a first flow of heat from the motor controller portion through the thermoelectric cooler to the thermally conductive element.

11. The method according to claim 10 further comprising detaching the battery pack from the surgical instrument, coupling the battery pack to a charging station, thermally coupling the thermoelectric cooler to an internal housing of the battery pack, reversing the first polarity and creating a second flow of heat from the internal housing through the thermoelectric cooler to the thermally conductive element.

\* \* \* \* \*